United States Patent
Karasic et al.

(10) Patent No.: US 11,903,593 B2
(45) Date of Patent: Feb. 20, 2024

(54) ANCHOR DELIVERY SYSTEM

(71) Applicant: Smith & Nephew, Inc., Memphis, TN (US)

(72) Inventors: Geoffrey Ian Karasic, Milton, MA (US); Nehal Navinbhai Patel, Boston, MA (US); Marc Joseph Balboa, Hopkinton, MA (US); Matthew Edwin Koski, Westford, MA (US); Benjamin Hall, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 283 days.

(21) Appl. No.: 17/526,044

(22) Filed: Nov. 15, 2021

(65) Prior Publication Data

US 2022/0071640 A1 Mar. 10, 2022

Related U.S. Application Data

(62) Division of application No. 16/623,474, filed as application No. PCT/US2018/039024 on Jun. 22, 2018, now Pat. No. 11,202,643.

(60) Provisional application No. 62/523,447, filed on Jun. 22, 2017, provisional application No. 62/523,442, filed on Jun. 22, 2017.

(51) Int. Cl.
| | |
|---|---|
| A61B 17/16 | (2006.01) |
| A61B 17/17 | (2006.01) |
| A61B 17/04 | (2006.01) |
| A61B 17/00 | (2006.01) |

(52) U.S. Cl.
CPC ...... *A61B 17/1631* (2013.01); *A61B 17/1796* (2013.01); *A61B 17/0401* (2013.01); *A61B 17/1633* (2013.01); *A61B 2017/00309* (2013.01); *A61B 2017/00862* (2013.01); *A61B 2017/0409* (2013.01); *A61B 2017/0414* (2013.01)

(58) Field of Classification Search
CPC .................. A61B 17/0401; A61B 17/1631
See application file for complete search history.

(56) References Cited

U.S. PATENT DOCUMENTS

| | | | | |
|---|---|---|---|---|
| 4,265,231 A | * | 5/1981 | Scheller, Jr. | ...... A61B 17/32002 606/103 |
| 4,541,423 A | * | 9/1985 | Barber | ............... A61B 17/1642 606/103 |

(Continued)

OTHER PUBLICATIONS

Japanese Application No. 2019-566697 Decision of Rejection dated Dec. 2, 2022.

(Continued)

*Primary Examiner* — Christian A Sevilla
(74) *Attorney, Agent, or Firm* — Burns & Levinson, LLP; Joseph M. Maraia; Marlo Schepper Grolnic

(57) ABSTRACT

An anchor delivery system includes both a straight and curved drill guide along with a flexible drill, a flexible obturator and a flexible anchor inserter. The curved drill guide has a distal tip with approximately a 15° bend from the primary axis of the drill guide. Both the drill and the obturator have a reduced diameter section to improve flexibility during passage through the curved drill guide. Additionally, a surface of the inserter shaft has a laser cut pattern which permits flexing of the inserter around the inner diameter of the curved drill guide.

15 Claims, 10 Drawing Sheets

(56) References Cited

U.S. PATENT DOCUMENTS

| | | | |
|---|---|---|---|
| 8,821,494 B2* | 9/2014 | Pilgeram | A61B 17/0482 606/80 |
| 10,092,303 B2* | 10/2018 | Sorensen | A61B 17/1631 |
| 2008/0188854 A1* | 8/2008 | Moser | A61B 17/1631 606/80 |
| 2009/0149890 A1* | 6/2009 | Martin | A61B 17/1728 606/301 |
| 2011/0071545 A1* | 3/2011 | Pamichev | A61F 2/34 606/139 |
| 2013/0012951 A1* | 1/2013 | Linderman | A61B 17/8855 606/93 |
| 2014/0107657 A1* | 4/2014 | Norton | A61B 17/88 606/232 |

OTHER PUBLICATIONS

Australian Application No. 2018290346 Examination Report dated Feb. 17, 2023.
Japanese Application No. 2019-566697 Notice of Reasons for Rejection dated Jun. 20, 2022.

* cited by examiner

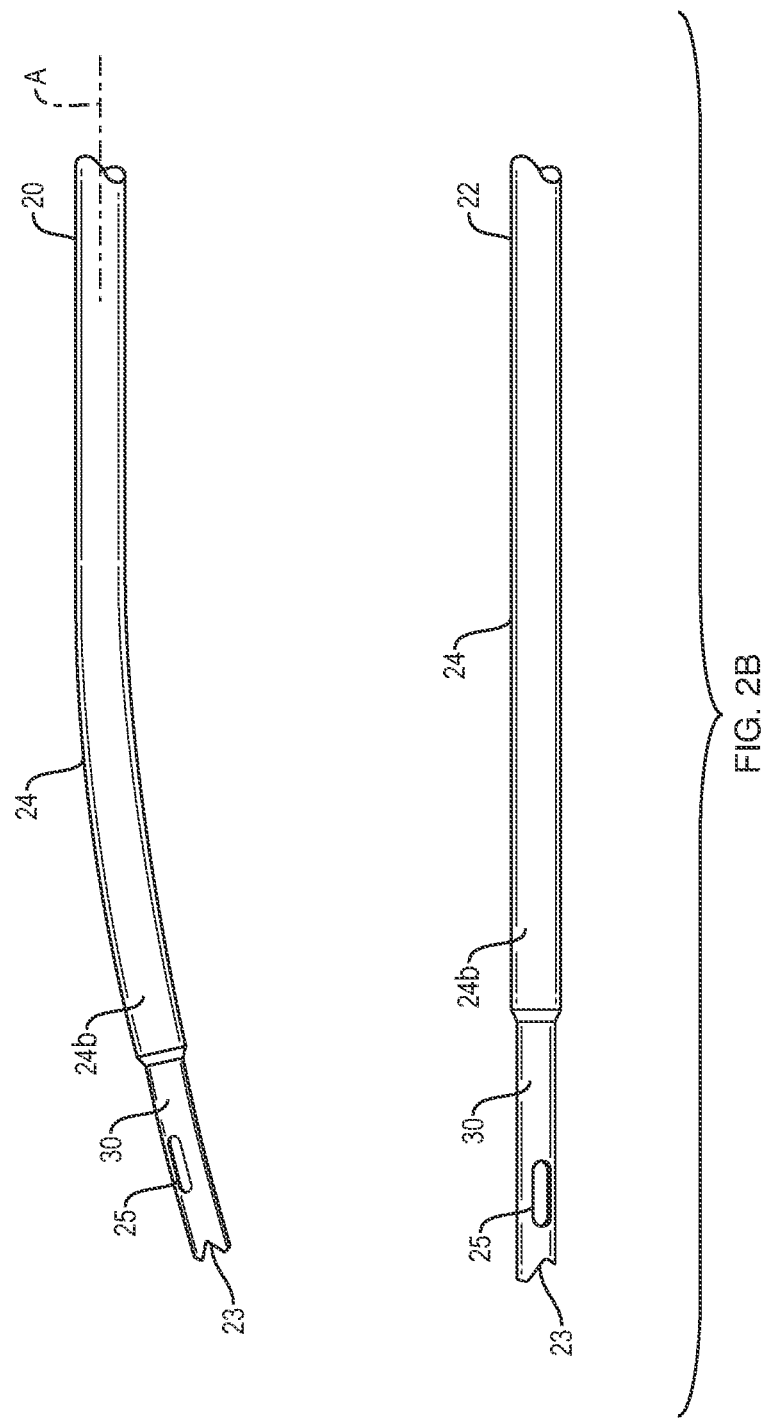

ANCHOR DELIVERY SYSTEM

CROSS-REFERENCE TO RELATED APPLICATIONS

This application is a divisional of U.S. application Ser. No. 16/623,474, entitled ANCHOR DELIVERY SYSTEM, which is the U.S. national phase entry under 35 U.S.C. § 371 of International Application No. PCT/US2018/039024, filed Jun. 22, 2018, entitled ANCHOR DELIVERY SYSTEM, which in turn claims priority to and benefit of U.S. Provisional Application No. 62/523,442, filed Jun. 22, 2017, and U.S. Provisional Application No. 62/523,447, filed Jun. 22, 2017, the contents of which are incorporated herein by reference in their entirety for all purposes.

FIELD

The present disclosure relates to methods and devices for use in surgical procedures and, more specifically, to arthroscopic methods and systems for inserting a suture anchor into bone.

BACKGROUND

Medical devices, such as suture anchors, have been developed for attaching soft tissue to bone. A suture anchor is typically inserted into and fixed within a bone hole drilled into bone at a surgical repair site. Sutures are typically coupled to the anchor and are used to secure the soft tissue to the bone to effect the repair. For many repair procedures, accuracy in the placement of suture anchors in bone is required to achieve consistently positive surgical outcomes, requiring substantial skill on the part of the surgeon.

Accurate placement of bone holes and suture anchors can be particularly challenging when repair is performed arthroscopically, as both access to and visibility of an arthroscopic surgical site may be more limited than is the case with open surgical procedures. For example, accurately drilling bone holes and placing suture anchors into these holes, at certain joint areas of the body, can be difficult for even a very experienced surgeon. This is due to the inability of the delivery devices to reach a preferred anchor delivery point or a preferred anchor trajectory, or both. One solution has been to provide curved drill guides to access locations and trajectories that would be difficult or impossible to access using straight in-line instruments. Most existing curved drill guides have cannulated shafts with varying degrees of curvature to guide passing instruments along a desired path. However, use of curved drill guides also necessitates the use of auxiliary curved instrumentation, such as a drill, an obturator, and/or an anchor inserter.

SUMMARY

Disclosed herein is an anchor delivery system which includes both a straight and curved drill guide along with a flexible drill, a flexible obturator and a flexible anchor inserter. The curved drill guide has a distal tip with approximately a 15° bend from the primary axis of the drill guide. Both the drill and the obturator have a reduced diameter section to improve flexibility during passage through the curved drill guide. Additionally, a surface of the inserter shaft has a laser cut pattern which permits flexing of the inserter around the inner diameter of the curved drill guide. Each of these adaptations advantageously allows the instruments to be used with both the straight and curved guides to achieve a wider range of access and trajectories during arthroscopic procedures.

Further examples of the anchor delivery system of this disclosure may include one or more of the following, in any suitable combination.

Examples of the anchor delivery system of this disclosure include a guide for insertion into a repair site, the guide having a central passage extending therethrough. A distal portion of the guide is curved relative to a longitudinal axis of the guide. The system also includes an obturator insertable through the passage of the guide for blocking the passage during insertion of the guide into the repair site. The obturator includes a shaft having a flexible portion. A diameter of the flexible portion is selected to allow bending of the obturator so as to pass through the curve of the guide. The system further includes a drill insertable through the passage of the guide for forming a hole in a bone at the repair site. The drill including a shank having a flexible portion. A diameter of the flexible portion is selected to allow bending of the drill so as to pass through the curve of the guide. The system also includes an anchor delivery tool insertable through the passage of the guide for implanting an anchor into the hole. The anchor delivery tool includes an elongate member having a flexible portion. A surface of the flexible portion includes a plurality of cuts permitting flexing of the anchor delivery tool about the cuts so as to pass through the curve of the guide.

In further examples of the system, a tip of the guide is configured to stabilize the guide against the bone. The distal portion of the guide includes at least one aperture in the surface of the guide in communication with the central passage of the guide. In examples, an angle of the curve is about 15 degrees. The diameter of the flexible portion of the shaft of the obturator is selected to be smaller than a diameter of a non-flexible portion of the shaft. In examples, the obturator includes a conical, atraumatic tip. The diameter of the flexible portion of the shank of the drill is selected to be smaller than a diameter of a non-flexible portion of the shank. In examples, the shank of the drill comprises Nitinol. In examples, the flexible portion of the shank of the drill includes a series of necked-down regions for increasing flexibility of the flexible portion. In other examples, the flexible portion of the shank of the drill includes a series of lobes for providing a bearing surface and a reduced clearance space between the drill and the guide. The series of lobes are adjacent to a cutting portion formed on or attached to a distal end of the drill. In examples, a distal end the elongate member of the anchor delivery tool comprises an area of reduced diameter. In examples, the system further includes an anchor coupled to the anchor delivery tool via a suture routed through a channel of the delivery tool and through a transverse eyelet of the anchor.

Examples of a method of delivering an anchor to a repair site of this disclosure include passing an obturator through a passage of a guide, the obturator including a shaft having a flexible portion. A diameter of the flexible portion is selected to allow bending of the obturator so as to pass through a curve of the guide. The method also includes passing the obturator and the guide over a guide wire implanted in a bone, and placing the tip of the guide against the bone to stabilize the guide. The method further includes removing the obturator from the passage of the guide and inserting a drill through the passage of the guide to drill a hole in the bone. The drill includes a shank having a flexible portion. A diameter of the flexible portion is selected to allow bending of the drill so as to pass through the curve of the guide. The method also includes removing the drill from the passage of the guide and passing an anchor coupled to an anchor delivery tool through the passage of the guide. The anchor delivery tool includes an elongate member having a flexible portion. A surface of the flexible portion includes a plurality of cuts permitting flexing of the anchor delivery tool about the cuts so as to pass through the curve of the guide. Examples of the method also include inserting the anchor into the hole in the bone, implanting the guide wire in the bone, removing the anchor delivery tool from the passage of the guide.

Examples of an anchor delivery tool of this disclosure include an elongate member having a flexible portion. A surface of the flexible portion includes a plurality of cuts permitting flexing of the tool about the cuts so as to pass through a curve of the guide. In examples, a distal end the elongate member comprises an area of reduced diameter. Examples of the anchor delivery tool further include an anchor coupled to the tool via a suture routed through a channel of the tool and through a transverse eyelet of the anchor.

Examples of a drill apparatus of this disclosure include a drill shaft having a proximal end and distal end. The drill apparatus also includes a cutting portion formed on or attached to the distal end of the drill shaft. The drill apparatus also includes a plurality of lobes formed on the drill shaft adjacent to the cutting portion. An outer circumferential surface of each lobe has a bearing surface. The drill apparatus also includes a plurality of neck segments. Each of the neck segments is located between adjacent instances of the lobes and have a lesser diameter than the plurality of lobes.

In further examples of the drill apparatus, the proximal end of the drill shaft is configured for coupling to a drill. In examples, the drill shaft is made from nitinol. In examples, the drill shaft extends through the curved drill guide. In examples, the curved drill guide includes a handle and a guide shaft coupled to the handle. The guide shaft includes a distal portion angled relative to a longitudinal axis of the guide shaft. The distal portion includes an end having a serrated edge. In examples, the drill shaft further includes a counterbore positioned distally to the plurality of lobes. The counterbore defines a plurality of cutting elements. In examples, each of the plurality of cutting elements has a cutting angle of between about 90-115°.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 2A-D illustrate an exemplary straight guide and an exemplary curved guide of the anchor delivery system of FIG. 1;

DETAILED DESCRIPTION

Figure 1:
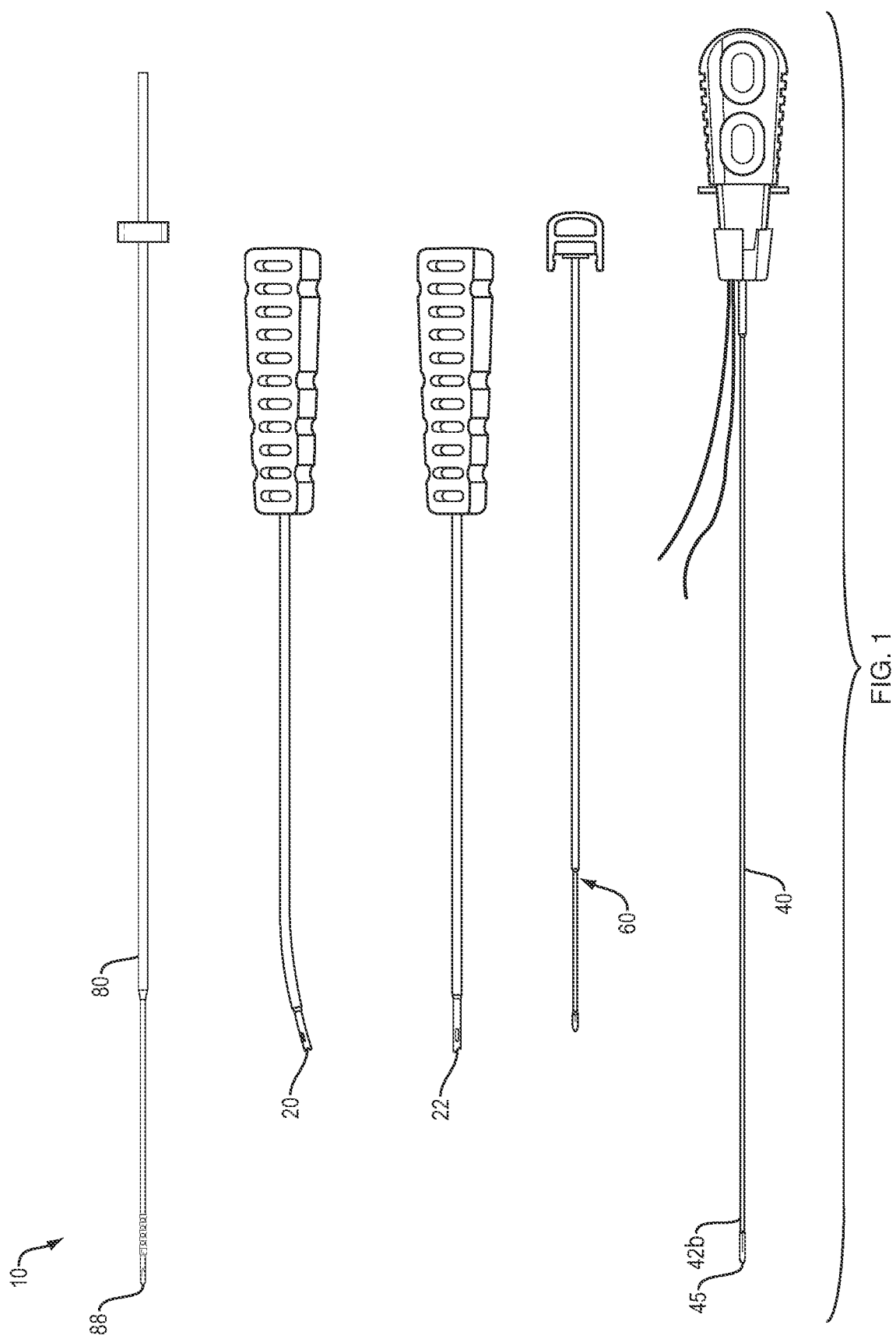
FIG. 1 illustrates an exemplary anchor delivery system of this disclosure.

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Referring now to FIG. 1, an exemplary anchor delivery system 10 of the present disclosure is illustrated. As shown in FIG. 1, the anchor delivery system 10 may include a curved guide 20 and a straight guide 22. A bend or curve is incorporated into curved guide 20 to direct passing instruments around anatomy during surgery, especially anatomy that prevents a straight trajectory. An anchor delivery tool 40 may also be provided which has a flexible shaft portion 42b. The anchor delivery tool 40 is capable of delivering an anchor 45, which may be a soft suture anchor, into a bone hole in a repair site of a patient. A flexible obturator 60 may also be provided and may be used for insertion through a passage extending through each of the guides 20 and 22. Finally, a flexible drill 80 may further be provided. A cutting portion 88 of the drill 80 may be capable of drilling a hole in bone for insertion of the anchor 45, as further described below.

Figure 2A:
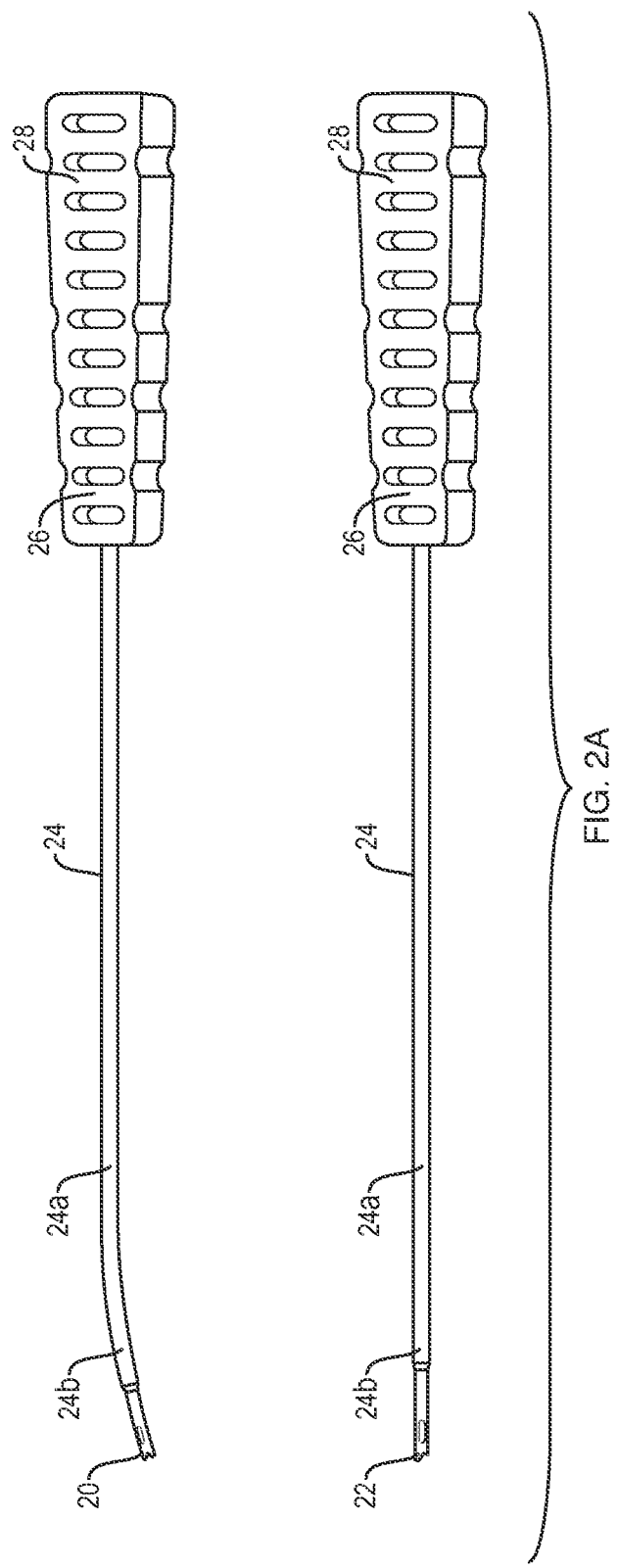

FIGS. 2A and 2B illustrate in further detail the curved guide 20 and the straight guide 22 of the present disclosure. Both of the guides 20, 22 may comprise a high-strength material, such as stainless steel, in order to substantially reduce the possibility of plastic deformation of the guides 20, 22 when subjected to various bending forces during surgery. However, other high-strength material known to one of ordinary skill in the art can be used. As shown in FIG. 2A, the guides 20, 22 each include a shaft 24 coupled to a handle 26. A central passage 32 (FIG. 2C) extends through the shaft 24 and the handle 26 for receiving the drill 80, the obturator 60 and the anchor delivery tool 40 of FIG. 1. The shaft 24 further includes a proximal portion 24a and a distal portion 24b. The proximal portion 24a is coupled to the handle 26 and extends distally from the handle 26. In examples, the handle 26 is slightly tapered toward the shaft 24 and includes ribs 28 along a length of the handle 26 for maintaining a grip on the handle 26 while imparting axial compression and bending into the guides 20, 22 during surgery. However, other means for maintaining a grip, known to one of ordinary skill in the art, may be used.

In FIG. 2B, it can be seen that the distal portion 24b of the shaft 24 includes an area of reduced diameter 30 terminating in a tip 23 configured for stabilizing the guide 20, 22 against bone. The distal portion 24b may also include at least one open side window 25. For the purposes of this disclosure, there are two windows 25 formed on opposite sides of the shaft 24. However, there may be more or fewer than two windows 25. The windows 25 may be useful for viewing depth markings on a surface of the passing instruments shown in FIG. 1. In examples, the windows 25 are located as distally as possible along the shaft 24, since the space to view them arthroscopically is small in some joints (such as the hip). In other examples, the windows 25 may be located more or less distally along the shaft 24. As seen in FIG. 2B, the distal portion 24b of the curved guide 20 is bent or curved relative to the longitudinal axis A of the curved guide 20. In examples, the angle of the bend or curve is about 15°.

Figure 2D:
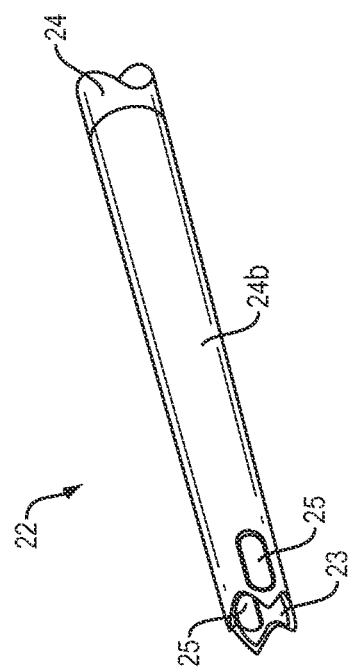
Figure 2C:
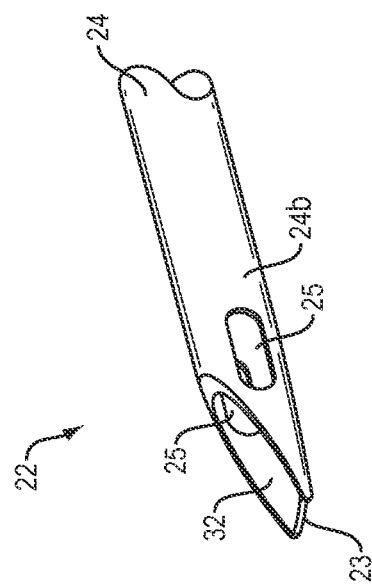

FIGS. 2C and 2D show examples of the tip 23 of the guide 20, 22 (shown as straight guide 22 for illustrative purposes). Specifically, the distal portion 24b of the guide 20, 22 as shown in FIG. 2C includes a forked tip 23 and an open side window 25 in communication with the central passage 32 of the guide 20, 22. Similarly, the guide 20, 22 as shown in FIG. 2D includes a crown-shaped tip 23 and open side windows 25. Other convenient shapes may be used for the tip 23 of the distal portion 24b of the shaft 24, the shape being selected to help stabilize the guide 20, 22 against bone.

Figure 3A:
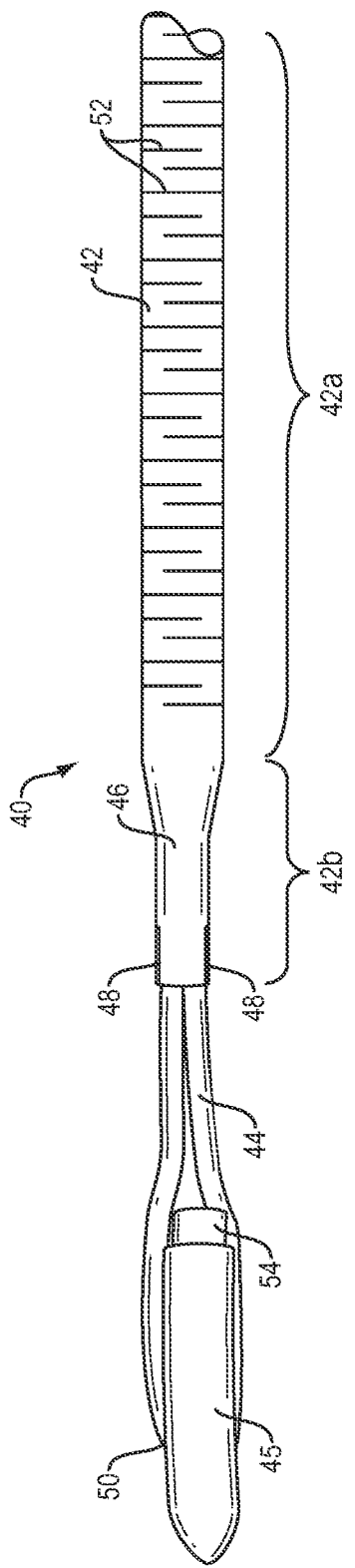
FIGS. 3A and 3B illustrate an exemplary suture anchor and an exemplary anchor delivery tool of the anchor delivery system of FIG. 1.

FIG. 3A illustrates examples of the anchor delivery tool 40 and the anchor 45 of the present disclosure. The anchor delivery tool 40 includes a shaft 42 and a handle (FIG. 1) coupled to the shaft 42. In examples, the shaft 42 and the handle may be assembled by heat staking, ultrasonic staking, spin welding, insert molding, or other methods known to one of ordinary skill in the art. The shaft 42 comprises stainless steel, but may be made from another biocompatible material known to one of ordinary skill in the art. Also, for the purposes of this disclosure, the handle may include suture retaining features for retaining a repair suture 44.

Figure 3B:
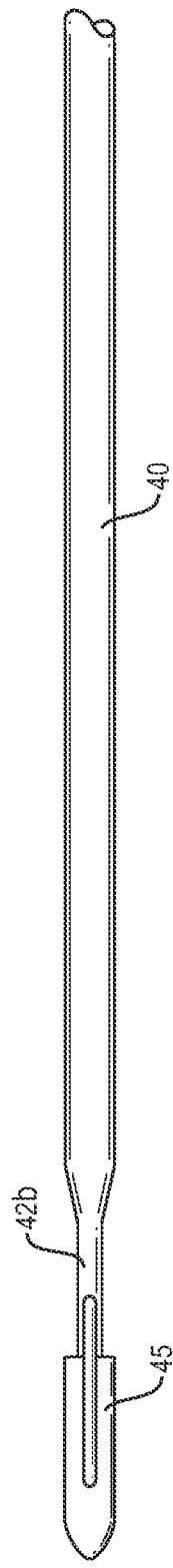

The shaft 42 includes a proximal portion 42a and a tapered-down distal portion 42b. The distal portion 42b comprises an area of reduced diameter 46 which is used for depth stop and relief purposes, as will be further described below. A surface of the proximal portion 42a further comprises a laser cut pattern 52 which permits flexing of the proximal portion 42a around the curve of the curved guide 20. As shown in FIG. 3A, the anchor 45 is disposed on a proximally-extending boss 54. The repair suture 44 extends through a cannulation of the shaft 42 and through opposing slots 48 in the distal portion 42b of the shaft 42. The repair suture 44 is also routed through a transverse eyelet 50 of the suture anchor 45. When the repair suture 44 is pulled proximally by the handle, the boss 54 is pulled inside the distal portion 42b of the shaft 42 such that the anchor 45 abuts the distal end of the distal portion 42b and is coupled to the delivery tool 40, as shown in FIG. 3B.

Figure 4:
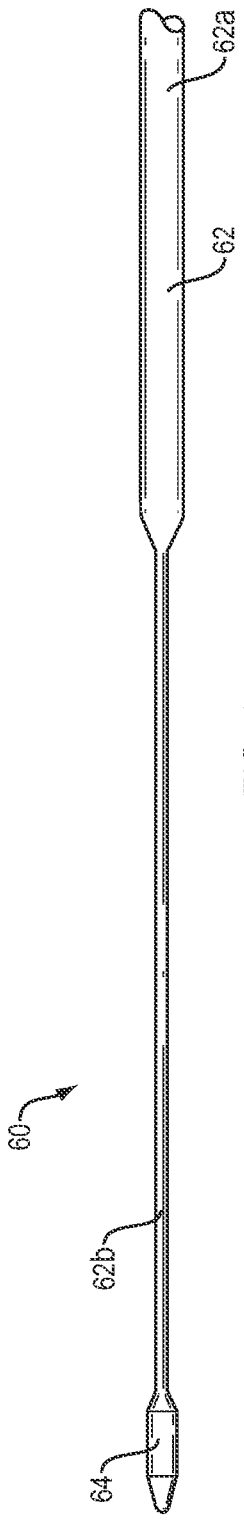
FIG. 4 illustrates an exemplary obturator of the anchor delivery system of FIG. 1.

FIG. 4 illustrates an exemplary obturator 60 that allows for easier percutaneous introduction of the guide 20, 22 to a desired site within the body by filling the inner diameter of the central passage 32 of the guide 20, 22 and substantially reducing the possibility of the tip 23 of the guide 20, 22 becoming caught on tissue within the body. The obturator 60 includes a shaft 62 coupled to a handle (FIG. 1). In examples, the shaft 62 and the handle of the obturator 60 are made from stainless steel and plastic, respectively. However, either one could be made from any other biocompatible material known to one of ordinary skill in the art. The shaft 62 may be cannulated for passing over a guide wire, as further described below. The shaft 62 includes a proximal portion 62a and a tapered-down distal portion 62b. A diameter of the distal portion 62b is selected to be smaller than a diameter of the proximal portion 62a to improve flexibility during insertion into the curved guide 20. Specifically, the distal portion 62b allows the shaft 62 to bend along the angled distal portion 24b of the curved guide 20 when the shaft 62 is inserted through the guide 20. The distal portion 62b of the obturator 60 may include a conical, atraumatic tip 64 for easier passage of the obturator 60 through the body. In other examples, not shown, the obturator 60 may have a sharp tip 64 allowing for easier and quicker insertion of the guide 20, 22 into the body.

Figure 5A:
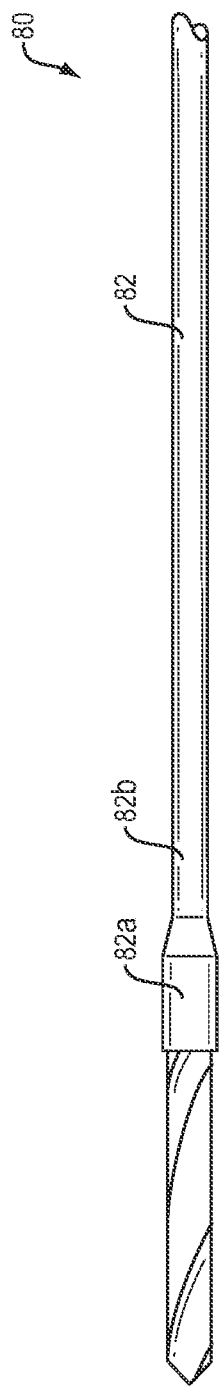
FIG. 5A illustrates a low friction bearing surface provided by a shoulder portion of a drill shaft according to an aspect of the present disclosure.

FIG. 5A shows an exemplary drill 80 for drilling a bone hole in bone. In an illustrative example of the drill 80, a low friction bearing surface may be provided by a shoulder portion 82a of a drill shaft 82. The shoulder portion 82a provides reduced clearance between the shaft 82 and the drill guide 20, 22 in which it is installed to maintain centering of the drill shaft 82 with respect to the inside diameter of the drill guide 20, 22. A necked down portion 82b of the shaft 82 provides flexibility that allows the shaft 82 to extend through bends in a curved drill guide 20.

Figure 5B:
FIG. 5B illustrates a low friction bearing surface provided by one or more sleeve portions that extend around portions of a drill shaft according to an aspect of the present disclosure.

Referring to FIG. 5B, in another illustrative example, a low friction bearing surface may include one or more sleeve portions 84 that extend around portions of the shaft 82. The sleeve portions 84 are operative to further reduce friction between the shaft 82 and the drill guide 20, 22 and to center the drill shaft 82 relative to the drill guide 20, 22. According to aspects of the present disclosure, the drill shaft 82 may be made of steel, nitinol or other metals. The sleeve portions 84 may be made of a plastic heat shrink material such as PEEK or PTFE, for example. In examples, the sleeve portions 84 may comprise plastic members that are press-fit or over-molded over the drill shaft 82. The bearing material can be fiber reinforced to provide extra rigidity, for example. The coefficient of friction between the plastic sleeve portions 84 and an inner surface of the metal drill guide 20, 22 is lower than between a metal surface of the drill shaft 82 and a metal inner surface of the drill guide 20, 22. In other examples, the low friction bearing surface and/or the drill guide 20, 22 may be made from materials such as dissimilar metals with improved frictional properties to reduce particulate generation. According to another aspect of the present disclosure, the low friction bearing surface may include one or more separately created bearings that are later assembled onto the drill shaft 82.

In the examples shown in FIGS. 5A and 5B, the low friction bearing surface takes up clearance space between the drill 80 and the drill guide 20, 22 to center the drill shaft 82 within the guide 20, 22, which improves alignment between the drill trajectory and the guide 20, 22. The reduced friction provided between the drill shaft 82 and the drill guide 20, 22 also allows a smoother motion of the drill shaft 82 within the drill guide 20, 22, which improves controllability of the drill 80. The reduced friction also reduces particulate generation, which can be harmful in a surgical environment.

Figure 5C:
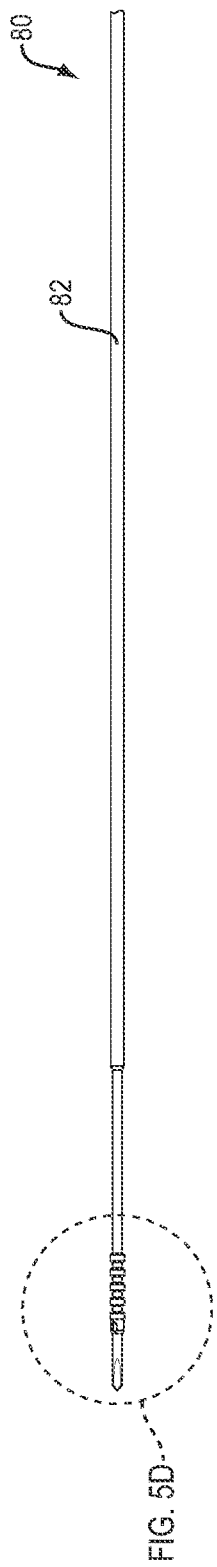
FIGS. 5C and 5D illustrate a drill shaft having a low friction bearing surface provided by a series of lobes and necked down regions according to an aspect of the present disclosure.
Figure 5D:
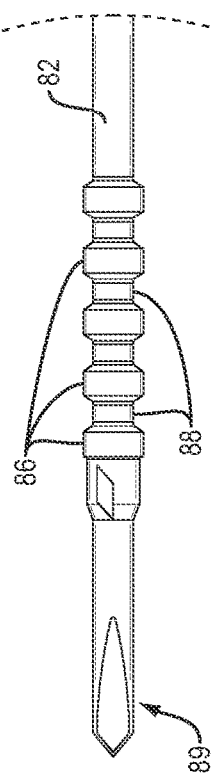
Figure 5E:
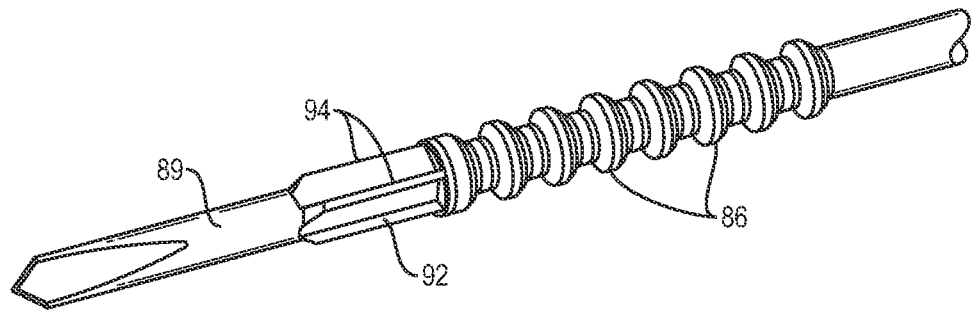
FIGS. 5E and 5F illustrate an example of a counterbore of the drill shaft of FIG. 5C.
Figure 5F:
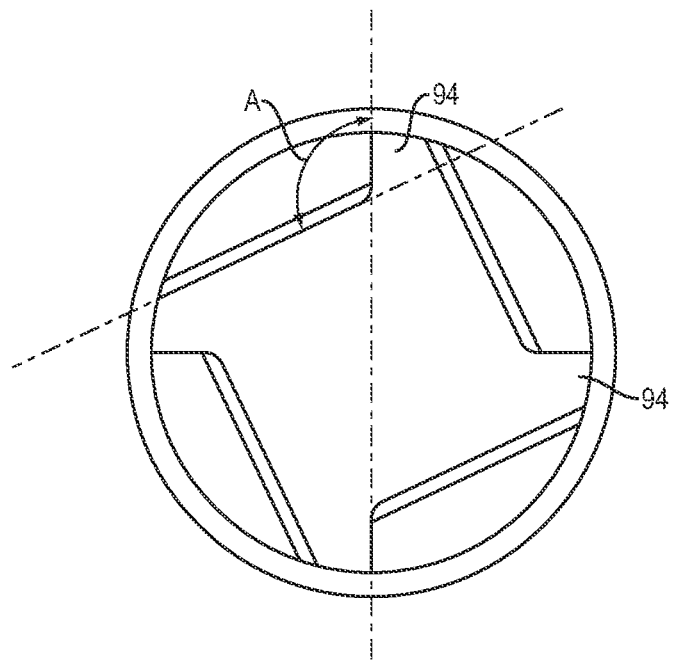

Referring now to FIG. 5C, according to another aspect of the drill 80 of the present disclosure, a drill shaft 82 includes a series of lobes 86 and necked down regions 88. The necked down regions 88 increase flexibility of the drill shaft 82. The series of lobes 86 are located along the drill shaft 82 to provide a bearing surface between the drill shaft 82 and the drill guide 20, 22. In an illustrative example, the lobes 86 are adjacent a cutting portion 89 that is formed on or attached to the distal end of the drill shaft 82. The lobes 86 can vary in number, size shape and spacing. The lobes 86 also provide reduced clearance space between the drill shaft 82 and the drill guide 20, 22. The reduced clearance increases alignment of the trajectory of the drill shaft 82 within the drill guide 20, 22. When the series of the lobes 86 are located within the drill guide 20, 22, spacing between the lobes 86 and the inner surface of the drill guide 20, 22 reduces cocking of the drill 80 as it exits the guide 20, 22. The necked down regions 88 between the lobes 86 have reduced cross sectional area and thus lower the area moment of inertia of the drill shaft 82. Deflection required for the drill shaft 82 to pass through a curved drill guide 20 is provided by the reduced area moment of inertia in the necked down region 88. This allows the drill shaft 82 to bend with less force than a conventional drill shaft. Friction between the drill shaft 82 and the drill guide 20, 22 is also reduced due to the improved flexibility provided by the necked down regions 88 of the drill shaft 82. FIGS. 5D and 5E illustrate an example of a counterbore 92 of the drill shaft 82 located distally to the series of lobes 86. The counterbore 92 can be used to undercut the cutting portion 89 for reduction of the drilling force needed to move the drill 80 in hard bone media. In examples, each of a plurality of cutting elements 94 defined by the counterbore 92 have a cutting angle A of between about 90-115° to allow for bone chip removal.

Figure 6A:
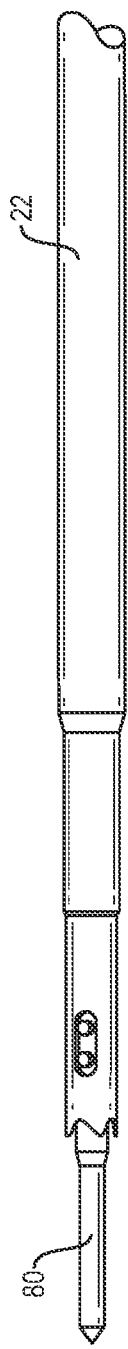
FIGS. 6A and 6B illustrate the drill/guide interface of the anchor delivery system of FIG. 1.
Figure 6B:
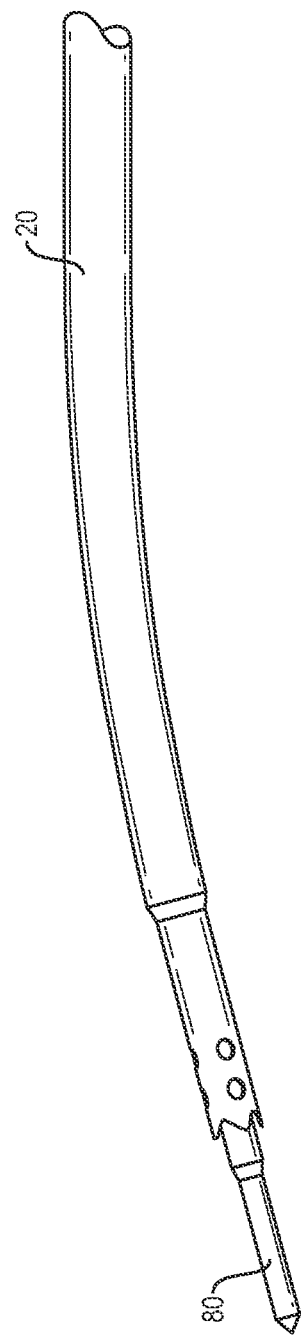

Although aspects of the present disclosure describe a drill shaft 82 having a series of lobes 86 and necked down regions 88 to reduce the area moment of inertia of the shaft 82 to increase flexibility of the drill 80, persons having ordinary skill in the art should understand that other examples of the disclosed drill 80 may include other geometries that change the area moment of inertia of the shaft 82 to increase flexibility of the drill shaft 82. According to another aspect of the present disclosure, flexibility of the drill 80 may be achieved via collapsible geometries that permit deflection or portions of the drill shaft 82. As shown in FIGS. 6A and 6B, whether the drill 80 exits the straight guide 22 (FIG. 6A) or the curved guide 20 (FIG. 6B), the drill 80 is aligned with the trajectory of the guide 20, 22.

Figure 7A:
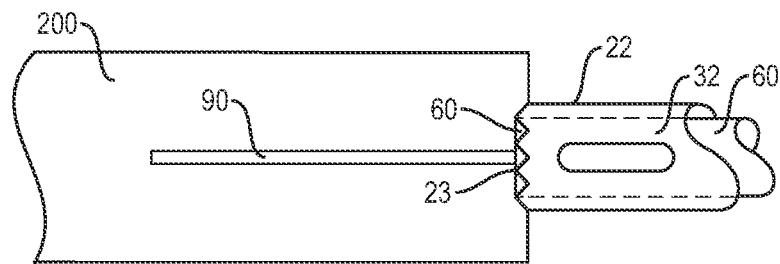
FIGS. 7A-C illustrate a method of delivering a suture anchor into a bone hole using the anchor delivery system of FIG. 1.

Turning now to FIG. 7A, in use, the obturator 60 is inserted through the central passage 32 of the guide 20, 22 (shown for exemplary purposes as straight guide 22) and the combination is then passed over a guide wire 90 previously implanted in bone 200 at the desired site for tissue repair. Once the guide 20, 22 reaches the desired site, the tip 23 of the guide 20, 22 is placed against the bone 200 to stabilize the guide 20, 22 for subsequent drilling and delivery of the suture anchor 45. The guide wire 90 is then removed from the bone 200 and the obturator 60 is removed from the central passage 32 of the guide 20, 22.

Figure 7B:
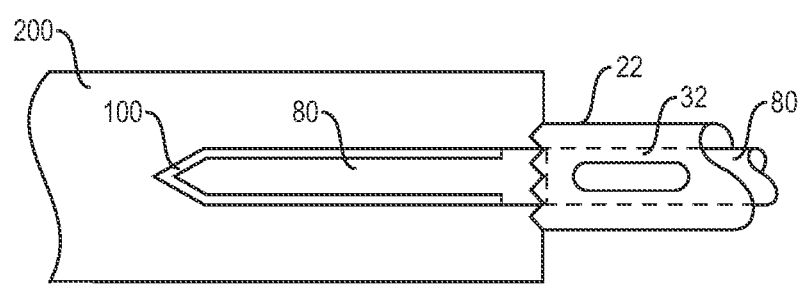
Figure 7C:
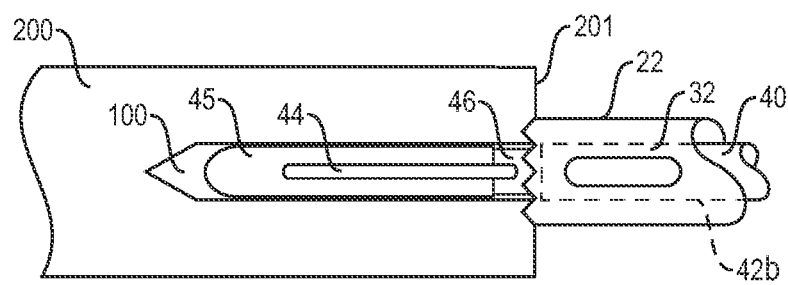

As shown in FIG. 7B, after removal of the obturator 60 from the guide 20, 22, the drill 80 is inserted into the central passage 32 of the guide 20, 22 and a drive unit (not shown) is coupled to the drill 80. The drive unit is operated to rotate the drill 80 to drill a hole 100 in the bone 200. The drill 80 is then removed from the central passage 32 of the guide 20, 22. Next, as shown in FIG. 7C, the anchor delivery tool 40 is disposed within the central passage 32 of the guide 20, 22 for delivery of the anchor 45 into the previously-drilled hole 100. The anchor 45 is advanced into the hole 100 in an axially-oriented manner by tapping on a proximal portion of the handle (not shown) of the anchor delivery tool 40. When full advancement occurs, the proximal portion of the anchor 45 is positioned below a surface 201 of the bone 200. Advantageously, the area of reduced diameter 46 included on the distal portion 42b of the anchor delivery tool 40 substantially reduces the possibility of the distal portion 42b getting stuck in the hole 100 of the bone 200 during delivery of the anchor 45. However, the area of reduced diameter 46 can also serve as a depth stop to ensure that the proximal portion of the anchor 45 is positioned a correct distance below a surface 201 of the bone 200. Once the anchor 45 has been delivered into the bone 200, the two free ends the repair suture 44 are released from the anchor delivery tool 40. The anchor delivery system tool 40 is subsequently removed from the body, thereby leaving the anchor 45 and the repair suture 44 in the bone 200. The suture 44 is then used to secure a tissue (not shown) to the bone 200.

While this disclosure has been particularly shown and described with references to preferred examples thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A method of delivering an anchor to a repair site, the method comprising:
    passing an obturator through a passage of a guide comprising a curve, the obturator including a shaft having a flexible portion, a diameter of the flexible portion selected to allow bending of the obturator so as to pass through the curve of the guide;
    passing the obturator and the guide over a guide wire implanted in a bone;
    placing the tip of the guide against the bone to stabilize the guide;
    removing the obturator from the passage of the guide;
    inserting a drill through the passage of the guide to drill a hole in the bone, the drill including a shank having a flexible portion, a diameter of the flexible portion selected to allow bending of the drill so as to pass through the curve of the guide;
    removing the drill from the passage of the guide;
    passing an anchor coupled to an anchor delivery tool through the passage of the guide, the anchor delivery tool including an elongate member having a flexible portion, a surface of the flexible portion comprising a plurality of cuts permitting flexing of the anchor delivery tool about the cuts so as to pass through the curve of the guide; and
    inserting the anchor into the hole in the bone.

2. The method of claim 1, further comprising implanting the guide wire in the bone.

3. The method of claim 1, further comprising removing the anchor delivery tool from the passage of the guide.

4. The method of claim 1, wherein an angle of the curve of the guide is about 15 degrees.

5. The method of claim 1, wherein the diameter of the flexible portion of the shaft of the obturator is selected to be smaller than a diameter of a non-flexible portion of the shaft.

6. The method of claim 1, wherein the obturator includes a conical, atraumatic tip.

7. The method of claim 1, wherein the diameter of the flexible portion of the shank of the drill is selected to be smaller than a diameter of a non-flexible portion of the shank.

8. The method of claim 1, wherein the shank of the drill comprises Nitinol.

9. The method of claim 1, wherein the flexible portion of the shank of the drill includes a series of necked-down regions for increasing flexibility of the flexible portion.

10. The method of claim 1, wherein the flexible portion of the shank of the drill includes a series of lobes for providing a bearing surface and a reduced clearance space between the drill and the guide.

11. The method of claim 10, wherein the series of lobes are adjacent to a cutting portion formed on or attached to a distal end of the drill.

12. The method of claim 11, wherein the cutting portion defines a plurality of cutting elements, each of the plurality of cutting elements having a cutting angle of between about 90-115°.

13. The method of claim 1, wherein a distal end of the elongate member of the anchor delivery tool comprises an area of reduced diameter.

14. The method of claim 1, further comprising coupling the anchor to the anchor delivery tool via a suture routed through a channel of the delivery tool and through a transverse eyelet of the anchor.

15. The method of claim 1, wherein the guide includes a handle and a guide shaft coupled to the handle.

\* \* \* \* \*